(12) United States Patent
Samant et al.

(10) Patent No.: US 11,975,219 B2
(45) Date of Patent: *May 7, 2024

(54) SYSTEMS AND METHODS FOR PARTICLE PORTAL IMAGING

(71) Applicant: University of Florida Research Foundation, Inc., Gainesville, FL (US)

(72) Inventors: Sanjiv Singh Samant, Gainesville, FL (US); Jyothier Nimmagadda, Gainesville, FL (US); James Edward Baciak, Gainesville, FL (US); Thomas S. S. Samant, Gainesville, FL (US); Andreas Jon Enqvist, Gainesville, FL (US)

(73) Assignee: UNIVERSITY OF FLORIDA RESEARCH FOUNDATION, INC, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/132,570

(22) Filed: Apr. 10, 2023

(65) Prior Publication Data

US 2023/0277873 A1 Sep. 7, 2023

Related U.S. Application Data

(63) Continuation of application No. 17/053,924, filed as application No. PCT/US2019/031623 on May 9, 2019, now Pat. No. 11,654,302.

(60) Provisional application No. 62/669,116, filed on May 9, 2018.

(51) Int. Cl.
A61N 5/10 (2006.01)

(52) U.S. Cl.
CPC ......... *A61N 5/1049* (2013.01); *A61N 5/1071* (2013.01); *A61N 2005/1054* (2013.01); *A61N 2005/1087* (2013.01)

(58) Field of Classification Search
CPC ............... A61N 5/1049; A61N 5/1071; A61N 2005/1054; A61N 2005/1087
See application file for complete search history.

(56) References Cited

U.S. PATENT DOCUMENTS

| | | |
|---|---|---|
| 6,519,316 B1 | 2/2003 | Collins |
| 7,502,443 B1 | 3/2009 | Haynes |
| 10,070,831 B2 | 9/2018 | Bennett |
| 2006/0017015 A1 | 1/2006 | Sliski et al. |
| 2008/0191142 A1 | 8/2008 | Pedroni |

(Continued)

OTHER PUBLICATIONS

International Search Report and Written Opinion dated Jul. 29, 2019 in co-pending PCT Application No. PCT/US2019/031623.

(Continued)

*Primary Examiner* — Sean M Luck
(74) *Attorney, Agent, or Firm* — Thomas | Horstemeyer, LLP

(57) ABSTRACT

A particle portal imaging (PPI) system and method are provided that can be used to provide a "beam's eye view" of a patient's anatomy as a charged particle beam is delivered to a target region of the patient's body. The PPI system is capable of performing real-time image acquisition and in-situ dose monitoring using at least exit neutrons generated within the patient. The PPI system can perform charged particle treatment (PT) monitoring to monitor the particle beam being used for PT.

20 Claims, 14 Drawing Sheets

(56) References Cited

U.S. PATENT DOCUMENTS

| | | |
|---|---|---|
| 2008/0203323 A1 | 8/2008 | Fehrenbacher et al. |
| 2009/0067576 A1 | 3/2009 | Maltz |
| 2010/0119032 A1 | 5/2010 | Yan et al. |
| 2010/0258732 A1* | 10/2010 | Rodriguez ........... A61N 5/1048 250/390.03 |
| 2011/0147608 A1 | 6/2011 | Balakin |
| 2011/0248188 A1 | 10/2011 | Brusasco et al. |
| 2013/0090547 A1 | 4/2013 | Bani-Hashemi |
| 2015/0071408 A1 | 3/2015 | Ebstein |
| 2016/0213951 A1 | 7/2016 | Uhlemann et al. |
| 2018/0188392 A1 | 7/2018 | Polf et al. |
| 2021/0286095 A1 | 9/2021 | Sauli et al. |

OTHER PUBLICATIONS

Charyyev, et al., "High quality proton portal imaging using deep learning for proton radiation therapy, a phantom study", Biomed Phys. Eng. Express 6 (2020) 035029, Apr. 2020.

Marafini, et al., "MONDA a neutron tracker for particle therapy secondary emission characterisation", Phys. Med. Biol. 62 3299, Aug. 2016.

Mares, et al., "A comprehensive spectrometry study of a stray neutron radiation field in scanning proton therapy", Phys. Med. Biol 61 4127, Apr. 2016.

Smelandytre-Hauge, et al., "A monte carlo feasibility study from neutron based real-time range verification in proton therapy", Scientific Reports, 9:2011, Feb. 2019.

* cited by examiner

SYSTEMS AND METHODS FOR PARTICLE PORTAL IMAGING

CROSS-REFERENCE TO RELATED APPLICATION

This application is a continuation claiming priority to, and the benefit of, co-pending U.S. application Ser. No. 17/053,924, filed Nov. 9, 2020, which is a U.S. National Phase application under 35 U.S.C. § 371 of PCT international application PCT/US2019031623 filed on May 9, 2019, which claims priority to, and the benefit of the filing date of, U.S. provisional application entitled, "Systems, Devices, and Methods for Imaging and Spectral Dosimetry using Exit Neutrons and Photons for Patients Undergoing Particle Beam Therapy," Ser. No. 62/669,116, filed on May 9, 2018, all of which are incorporated by reference herein in their entireties.

TECHNICAL FIELD

The present invention is generally related to charged particle therapy (PT), and more particularly, to methods and systems for particle portal imaging.

BACKGROUND

The fundamental goal in radiation therapy (RT) treatment planning, whether it be X-ray radiation therapy (XRT) or charged PT, is to maximize the dose delivered to the tumor while minimizing the dose delivered to the surrounding tissue. To fulfill this objective, intensity modulated radiation therapy (IMRT) is often utilized, in which complex beam sequences are delivered to the patient to generate sophisticated dose distributions that precisely target the tumor volume. However, the steep dose gradients in IMRT increase the risk of dose to surrounding organs from small shifts on the order of millimeters in patient position. This enhances the need for accurate localization of the target volume using image guidance systems or image guided radiation therapy (IGRT).

Charged PT methods such as proton therapy and heavy ion therapy (12C) hold the promise of significantly reduced toxicity to normal tissue while focusing the radiation on the tumor in a manner more precise than photon RT, even with advances made with 3-D conformal RT and IMRT. Charged PT offers a dosimetric advantage in improving the radiation dose to critical organs (e.g., heart, lung, and esophagus) as compared with IMRT using photons (high energy X-rays). With PT, however, real-time image guidance, which provides information on the position of the tumor target within the beam aperture, is hindered by the finite range of the charged particles, the very physical property that allows its therapeutic advantage over megavoltage X-rays.

A need exists for a way to monitor the proton beam used in PT to ensure that only intended targets are irradiated.

SUMMARY

The present disclosure is directed to a particle portal imaging (PPI) system and method. The PPI system comprises a charged particle beam source and an imaging system. The charged particle beam source generates a charged particle beam that is directed toward a target region of a body of a patient such that a spread out bragg peak (SOBP) is produced inside of the patient's body. The SOBP inside of the body produces at least exit neutrons. The imaging system comprises a radiation imager and a processor. The radiation imager is positioned to receive at least a portion of the exit neutrons and to generate one or more radiographic images from the exit neutrons. The processor is in communication with the radiation imager to receive the radiographic image(s) and is configured to perform one or more image processing algorithms that process the radiographic image(s) to obtain information about the patient.

In accordance with one aspect, the radiation imager is configured to perform a preferential selection process that selects the exit neutrons that are used to generate said one or more radiographic images based at least in part on energy levels of the exit neutrons.

In accordance with one aspect, the radiation imager comprises a converter, a mirror and an optical sensor. The converter receives at least the exit neutrons and converts them into light propagating in a first direction. The mirror receives the light propagating in the first direction and directs at least a portion of the received light in a second direction that is at a non-zero-degree angle to the first direction. The optical sensor receives at least a portion of the light propagating in the second direction. The optical sensor comprises an array of sensor elements, and each sensor element generates a respective electrical signal based on an amount of the light received thereby. Each radiographic image corresponds to a combination of the electrical signals generated by the sensor elements at a given time instant.

In accordance with one aspect, the converter is a scintillator.

In accordance with one aspect, the mirror is a forty-five-degree mirror, and the second direction is at a forty-five-degree angle to the first direction.

In accordance with one aspect, the optical sensor is a charge coupled device (CCD) sensor.

In accordance with another aspect, the optical sensor is a complementary metal oxide semiconductor (CMOS) sensor.

In accordance with one aspect, the radiation imager comprises a detector that receives the exit neutrons, forward momentum neutrons and/or photons and converts them into one or more radiographic images.

In accordance with one aspect, the charged beam source is a proton beam source that generates a proton beam.

In accordance with one aspect, the radiation imager generates a series of radiographic images, and each radiographic image of the series is captured at a different instant in time during the PT session. At least one of the image processing algorithms performed by the processor analyzes the radiographic images of the series to identify at least one particular feature that is present in each radiographic image of the series and to determine whether a position of the particular feature has changed over the different instants of time.

In accordance with one aspect, at least one image processing algorithm performed by the processor analyzes the radiographic image(s) to verify a geometry of the charged particle beam at the target region during a charged particle treatment (PT) session.

In accordance with one aspect, at least one image processing algorithm performed by the processor analyzes the radiographic image(s) to determine a radiation dose of the charged particle beam delivered to the target region during a PT session.

In accordance with one aspect, at least one image processing algorithm performed by the processor analyzes the radiographic image(s) to determine a radiation dose of the charged particle beam delivered to areas adjacent to the target region during a PT session.

In accordance with one aspect, the radiation imager is moved relative to the patient during the PT session to change an angle of the radiation imager relative to the charged particle beam, and a plurality of two-dimensional (2-D) radiographic images are captured by the radiation imager at different respective angles of the radiation imager relative to the charged particle beam. At least one image processing algorithm performed by the processor is a reconstruction algorithm that generates one or more three-dimensional (3-D) radiographic images from the 2-D radiographic images.

In accordance with one aspect, the charged particle beam comprises a pencil beam that is scanned through layers of the body of the patient during the PT session such that at least one 2-D radiographic image is generated by the radiation imager per scanned layer. An image processing algorithm performed by the processor combines the 2-D radiographs for all of the scanned layers and uses a proton beam energy associated with each scanned layer to generate a three-dimensional (3-D) radiographic image of the target region.

In accordance with one aspect, one image processing algorithm performed by the processor determines, based on the 3-D radiographic image, whether or not actual delivery of the charged particle beam to the target region met constraints of a treatment plan for an intended delivery of the charged particle beam to the target region.

In accordance with one aspect, one image processing algorithm performed by the processor determines, based on the 3-D radiographic image, whether a radiation dose delivered by the charged particle beam to the target region met constraints of a treatment plan for an intended radiation dose to be delivered during a PT session.

In accordance with one aspect, one image processing algorithm performed by the processor modifies, based on the 3-D radiographic image, a treatment plan associated with the patient.

The method for performing PPI comprises:
  with a charged particle beam source of a PPI system, generating a charged particle beam and directing the charged particle beam toward a target region of a body of a patient such that a spread out bragg peak (SOBP) is produced inside of the patient's body, the SOBP inside of the body producing at least exit neutrons;
  with a radiation imager of an imaging system of the PPI system, receiving at least a portion of the exit neutrons and generating one or more radiographic images from said at least a portion of the exit neutrons; and
  with a processor of the imaging system, receiving said one or more radiographic images and performing one or more image processing algorithms that process said one or more radiographic images to obtain information about the patient.

In accordance with one aspect of the method, the method further comprises: in the radiation imager, performing a preferential selection process that selects the exit neutrons that are used to generate said one or more radiographic images based at least in part on the energy levels of the exit neutrons.

These and other features and advantages of the inventive principles and concepts will become apparent from the following description, drawings and claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 6A shows the pulse shape discrimination (PSD) result taken with the He-4 gas detector at a PT facility; FIG. 6B shows the spectroscopic comparison of proton therapy data with other know neutron sources such as D-D, D-T and Cf-252.

DETAILED DESCRIPTION

Figure 1:
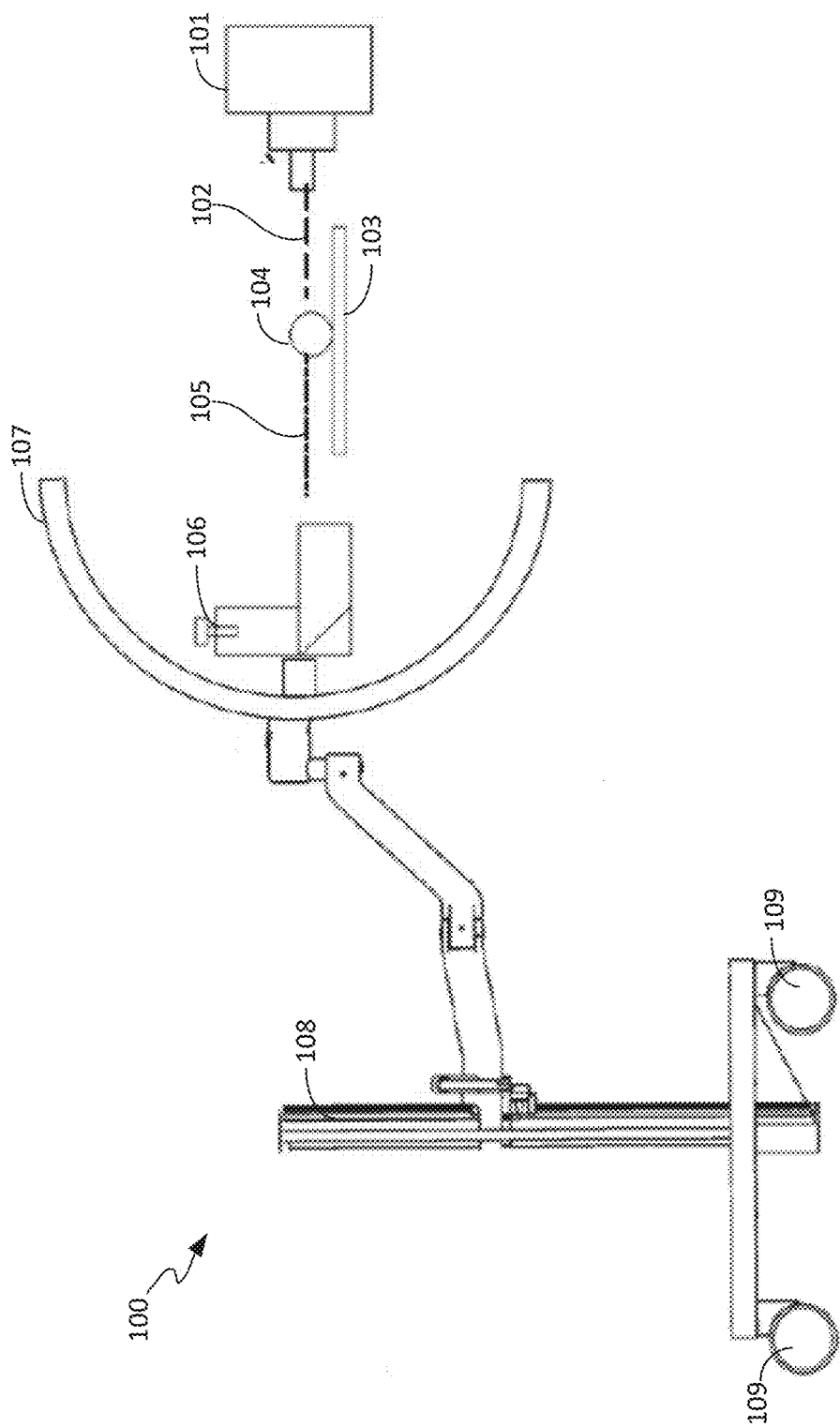
FIG. 1 is a schematic diagram of the PPI system in accordance with a representative embodiment.

The present disclosure is directed to a particle portal imaging (PPI) system and method that can be used to provide a "beam's eye view" of a patient's anatomy as a charged particle beam is delivered to a target region of the patient's body. The PPI system can perform real-time image acquisition and in-situ dose monitoring using at least exit neutrons generated within the patient. The PPI system can perform PT monitoring to monitor the particle beam being used for PT.

When a particle beam of high-energy ions, such as electrons, photons, protons, or heavy ions, is made incident on a target, sufficient secondary (i.e., exit) neutrons are generated from which the PPI system can generate radiographic images of the patient based at least on the exit neutrons generated within the Spread-Out Bragg Peak (SOBP) inside of the irradiated body. Other types of secondary radiation may also be generated, such as X-ray radiation, for example. The radiographic images generated using the secondary neutrons passing through the patient's body may be utilized for a variety of reasons, including to assess the dose to anatomical structures adjacent to the target region.

The PPI system, which delivers charged particle (e.g., proton) beams using passive scattering or active scanning (also known as pencil beam scanning or particle beam scanning (PBS)), may be used to generate a single "summed" image from the entire duration of the treatment beam, or streamed images during time intervals of the treatment beam. For passive scattering proton beams, 2-D radiographic images of the patient's anatomy using exit neutrons and/or photons are generated. In the case of 2-D radiographic images, they may also be taken in different orientations to reconstruct 3-D images. For PBS, each energy layer associated with the PBS beam delivery can be used to generate a 2-D image, and all the energy layers can then combined to generate a 3-D image of the region of the patient where the protons deposit energy and produce neutrons and xrays. These PPI base images can be color images or grayscale images similar to other scanning technologies, such as X-ray, ultra sound, gamma, etc.

The PPI system and method disclosed herein may also be used to determine the length, height, width, and/or volume of the cancer and/or organs within the patient. Additionally, the PPI system and method may be used to determine other aspects of the patient undergoing PT. For example, the PPI system and method may be used to verify the dose delivered to the tumor target and to identify and/or analyze additional features for clinical PT, as would be recognized by one of ordinary skill in the art having the benefit of this disclosure.

The imaging system of the PPI system includes a neutron and/or photon converter, such as a scintillator (for example, 6LiF—ZnS), or a detector (for example NOVA Scientific neutron sensitive micro channel plate (MCP) glass doped with 10B or Gd) or any other technology that converts neutrons/photons into signals. In embodiments in which the neutron and/or photon converter such as a scintillator is used, the converter converts the photons and/or neutrons into light and an optical sensor of the imaging system, such as a charge coupled device (CCD) sensor or complementary metal oxide semiconductor (CMOS) sensor converts the light into either color or grayscale images. This is an indirect conversion of neutrons and/or photons into color or grayscale images. In the case where a neutron and/or photon detector is used in the imaging system, the detector receives neutrons and/or photons and performs a direct conversion of the neutron and/or photons into an image. The term "radiation imager," as that term is used herein, is intended to denote both types of devices, i.e., devices that perform direct or indirect conversion of neutrons and/or photons into color or grayscale images. A combination of a scintillator and a CCD sensor is an example of a radiation imager that performs indirect conversion, whereas a neutron radiation detector, such as a He-4 gas detector, is an example of a radiation imager that performs direct conversion.

The scintillator or detector may be used in conjunction with a CCD/CMOS camera system using a mirror or optical fibers to direct the scintillator output to a sensor outside the direct path of the exit radiation, or overlaid on a flat panel detector, whereby the scintillator is placed directly onto the photodiode matrix of the flat panel system, for improved light collection efficiency to produce either color or grayscale images. The radiation imager may be positioned at any distance from the target and at any angle depending on the positioning of the patient. A shield can be placed between the imaging system and the cyclotron or synchrotron to remove or minimize the photons so that neutron images of the patient's anatomy are produced by the imaging system.

The PT source is typically a cyclotron or synchrotron, which is a particle accelerator commonly used as a source for the charged particle beam therapy. A cyclotron or synchrotron produces higher energy particles such as protons or 12C. These higher energy particles, during the interaction with matter, can produce secondary particles such as like neutrons, electrons, x-rays and gammas.

In accordance with a representative embodiment, the PPI system measures the spatio-spectral distribution of secondary neutrons generated in various locations within the patient's anatomy and in the beam collimators. By measuring the spatio-spectral distribution, one can achieve two highly important tasks. First, the unscattered neutrons would be what irradiate secondary organs significantly in the forward beam direction past the cancer irradiation target. Secondly, the scattered neutrons now have a new direction and energy indicating not only where but how much energy was deposited in specific organs. Using these two distinct neutron flux distributions, one can obtain significant additional understanding of secondary neutron-induced cancer risk.

Additionally, since the neutrons generated will be highly dependent not only on what the characteristics of a specific PT facility is, but also which type and where a specific cancer is located, this will allow significant improvements to be made in patient-by-patient impact and risk, and potentially be used as guidance for particle portal imaging. A neutron radiation detector, such as a He-4 gas detector, for example, may be used to measure the spatio-spectral distribution of the secondary neutrons. Knowledge of the spectral distribution of the secondary neutrons can be used to optimize the detector energy response. Knowledge of the proton beam characteristics and the neutron and/or photon spectra generated can be used to optimize the radiation imager, including composition and thickness of the scintillator. For example, using the neutron energy spectra, one can choose the neutron absorbing material for scintillation and its optimal thickness. This knowledge can be used to select materials for the scintillator that maximize light generation and collection, and to select scintillator material and imager geometry that maximizes selection of those exit neutron and xrays that produce best image quality based on spatial resolution and image contrast.

This PPI system and method apply to both passive spreading, in which one or more scatterers are used to produce a homogenous proton beam profile which is then incident on a compensator to generate a charged particle beam (e.g., proton beam) with the desired dose distribution in a patient; and active scanning or active spreading, in which magnetic fields are used to generate or "paint" the treatment volume, also known as intensity modulated proton therapy (IMPT) (the proton analogue to photon based intensity modulated radiation therapy (IMRT)), voxel by voxel in each layer, and in successive contiguous layers. The proton beam is incident to these contiguous layers.

In the following detailed description, for purposes of explanation and not limitation, exemplary, or representative, embodiments disclosing specific details are set forth in order to provide a thorough understanding of inventive principles and concepts. However, it will be apparent to one of ordinary skill in the art having the benefit of the present disclosure that other embodiments according to the present teachings that are not explicitly described or shown herein are within the scope of the appended claims. Moreover, descriptions of well-known apparatuses and methods may be omitted so as not to obscure the description of the exemplary embodiments. Such methods and apparatuses are clearly within the scope of the present teachings, as will be understood by those of skill in the art. It should also be understood that the word "example," as used herein, is intended to be non-exclusionary and non-limiting in nature.

The terminology used herein is for purposes of describing particular embodiments only and is not intended to be limiting. The defined terms are in addition to the technical, scientific, or ordinary meanings of the defined terms as commonly understood and accepted in the relevant context.

The terms "a," "an" and "the" include both singular and plural referents, unless the context clearly dictates otherwise. Thus, for example, "a device" includes one device and plural devices. The terms "substantial" or "substantially" mean to within acceptable limits or degrees acceptable to those of skill in the art. For example, the term "substantially parallel to" means that a structure or device may not be made perfectly parallel to some other structure or device due to tolerances or imperfections in the process by which the structures or devices are made. The term "approximately" means to within an acceptable limit or amount to one of ordinary skill in the art. Relative terms, such as "over," "above," "below," "top," "bottom," "upper" and "lower" may be used to describe the various elements' relationships to one another, as illustrated in the accompanying drawings. These relative terms are intended to encompass different orientations of the device and/or elements in addition to the orientation depicted in the drawings. For example, if the device were inverted with respect to the view in the drawings, an element described as "above" another element, for example, would now be below that element.

Relative terms may be used to describe the various elements' relationships to one another, as illustrated in the accompanying drawings. These relative terms are intended to encompass different orientations of the device and/or elements in addition to the orientation depicted in the drawings.

The term "memory" or "memory device," as those terms are used herein, are intended to denote a non-transitory computer-readable storage medium that is capable of storing computer instructions, or computer code, for execution by one or more processors. References herein to "memory" or "memory device" should be interpreted as one or more memories or memory devices. The memory may, for example, be multiple memories within the same computer system. The memory may also be multiple memories distributed amongst multiple computer systems or computing devices. More specific examples (a nonexhaustive list) of the computer-readable storage medium would include the following: an electrical connection (electronic) having one or more wires, a portable computer diskette (magnetic), a random access memory (RAM) (electronic), a read-only memory (ROM) (electronic), an erasable programmable read-only memory (EPROM or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory. In addition, the scope of the certain embodiments of the present invention includes embodying the functionality of the preferred embodiments of the present invention in logic embodied in hardware or software-configured mediums.

A "processor" or "processing device," as those terms are used herein encompass an electronic component that is able to execute a computer program or executable computer instructions. References herein to a system comprising "a processor" or "a processing device" should be interpreted as a system having one or more processors or processing cores. The processor may for instance be a multi-core processor. A processor may also refer to a collection of processors within a single computer system or distributed amongst multiple computer systems. The term "computer," as that term is used herein, should be interpreted as possibly referring to a single computer or computing device or to a collection or network of computers or computing devices, each comprising a processor or processors. Instructions of a computer program can be performed by a single computer or processor or by multiple processors that may be within the same computer or that may be distributed across multiple computers.

FIG. 1 is a schematic diagram of the PPI system 100 in accordance with a representative embodiment. During a PT treatment session, a charged particle beam (e.g., a proton beam, an electron beam, a photon beam, a heavy ion beam, etc.) 102 from a charged particle beam source 101, such as a cyclotron or synchrotron, for example, produces a spread out bragg peak (SOBP) inside of a patient 104 who is lying on a table 103. The SOBP inside of the patient 104 produces forward momentum neutrons 105, also referred to herein as exit neutrons 105. These exit neutrons 105 are then absorbed/collected by a radiation imager 106. For ease of discussion, it will be assumed that the radiation imager 106 is a scintillator, but direct conversion detectors of the type described above may instead be used.

In accordance with this representative embodiment, the radiation imager 106 is mounted on an arm 107 that can be rotated around the patient 104 to produce neutron images of the patient's anatomy at different angles in line with the charged particle beam 102. The arm 107 may be C-shaped, although it can have other shapes. The arm 107 is mechanically coupled to a stand 108, which will typically have wheels 109 to allow it to be easily positioned and moved.

Figure 2:
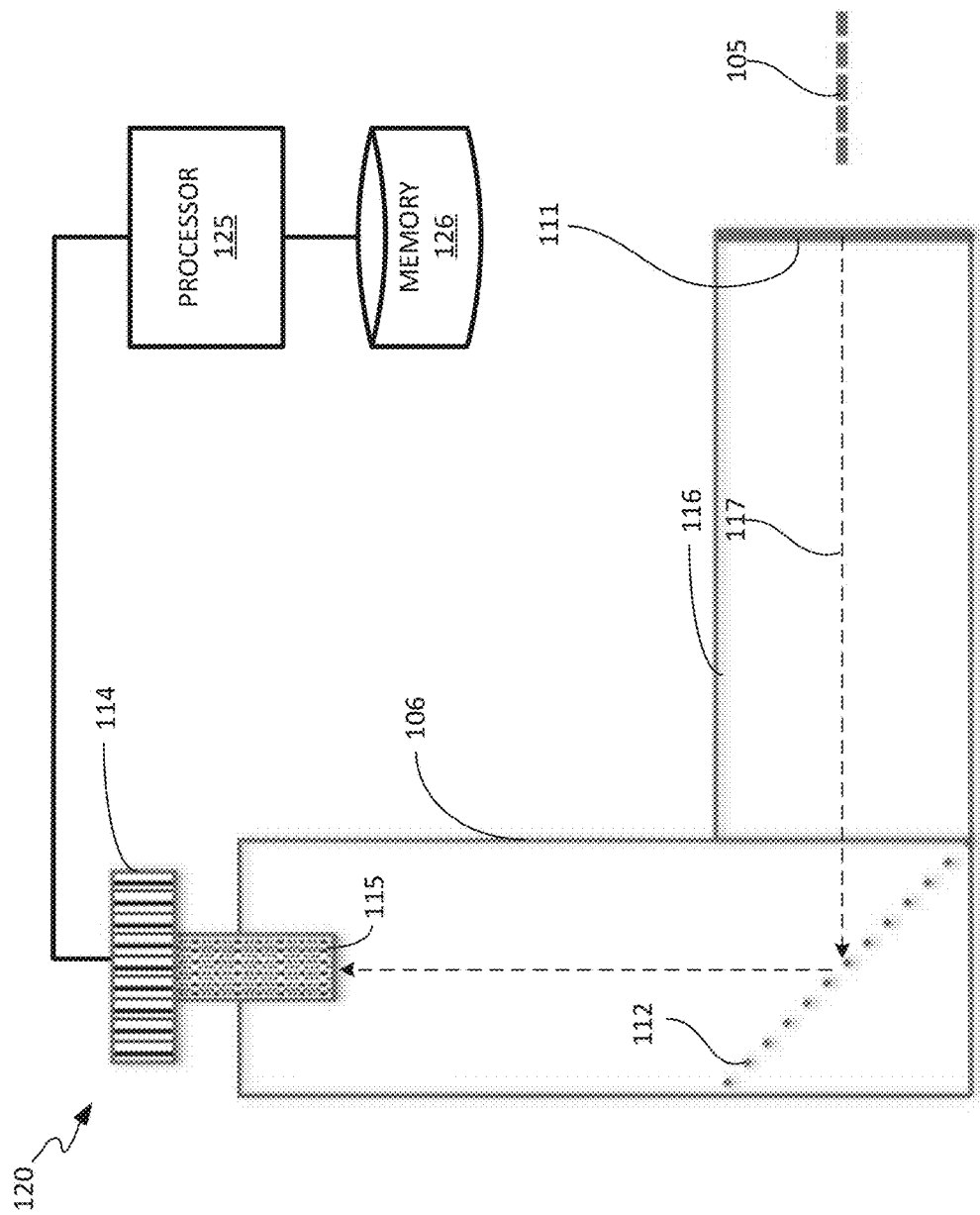
FIG. 2 is a block diagram of an imaging system of the PPI system shown in FIG. 1 in accordance with a representative embodiment.

FIG. 2 shows a block diagram of an imaging system 120 of the PPI system in accordance with a representative embodiment. The imaging system 120 comprises the radiation imager 106 shown in FIG. 1, a processor 125 and a memory device 126. The radiation imager 106 produces neutron images of the anatomy of the patient 104 (FIG. 1). In accordance with this representative embodiment, the exit neutrons 105 are received on the opposite side of the patient 104 from the source (not shown) by an indirect converter 111. As mentioned above, the radiation imager 106 may be a combination of an optical sensor (e.g., a CCD sensor) and a neutron-to-light converter, such as a scintillator, for example, that performs direct conversion of neutrons to images or it may be a detector, such as, for example, a NOVA Scientific neutron sensitive MCP or a He-4 gas detector that performs direct conversion of neutrons and/or photons into an image. For ease of discussion, it will be assumed that the radiation imager 106 comprises a neutron-to-light converter (e.g., a scintillator) 111 and an optical sensor 114 that act together to convert neutrons and/or photons into color or grayscale images. In accordance with a representative embodiment, the size of the scintillator is 200 millimeters (mm)×200 mm, although the inventive principles and concepts are not limited to the scintillator having any particular dimensions or configuration.

The converter 111 converts the exit neutrons 105 and/or photons into light 117, which is reflected by a 45° tilted mirror 112 toward an optical sensor 114. The reflected light is collected by the optical sensor 114, which may be, for example, a CCD sensor, a CMOS sensor or any other suitable optical sensor. The optical sensor 114 comprises an array of sensor elements, or pixels, each of which generates a respective electrical signal based on light received by the respective sensor element. These electrical signals together comprise an image of the anatomy of the patient 104 undergoing the treatment. The optical sensor 114 can be cooled with a cooling system (not shown) to reduce the number of isolated hot pixels. To maximize the amount of light that is received by the optical sensor 114, a lens 115 is typically disposed in between the optical sensor 114 and the mirror 112. This entire setup may be enclosed in a light tight L-shaped box 116.

Figure 3:
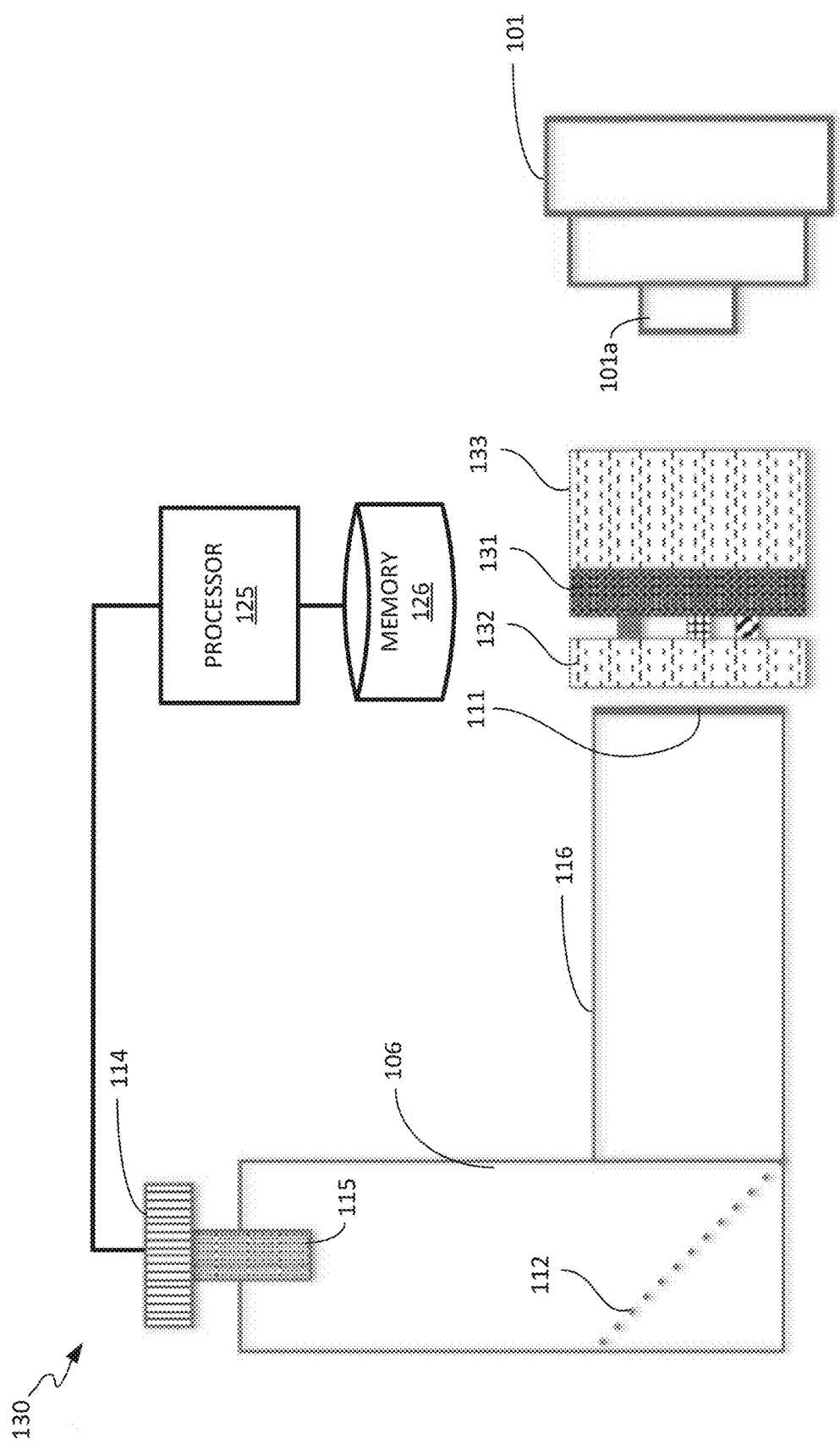
FIG. 3 shows a schematic diagram of the imaging system of the PPI system in accordance with a representative embodiment in which a tissue equivalent phantom is imaged.

FIG. 3 shows a schematic diagram of the imaging system 130 of the PPI system in accordance with a representative embodiment in which a tissue equivalent phantom 131 is imaged. Like the imaging system 120 shown in FIG. 2, the imaging system 130 comprises the radiation imager 106, the processor 125 and the memory device 126. The tissue equivalent phantom 131 is sandwiched between solid water phantoms 132 and 133. The solid water phantoms 132, 133 are disposed in between the radiation imager 106 and the charged particle beam snout 101a of the charged particle beam source 101 such that the forward scattered spallation neutrons will be incident on the converter 111 of the radiation imager 106.

Figure 4:
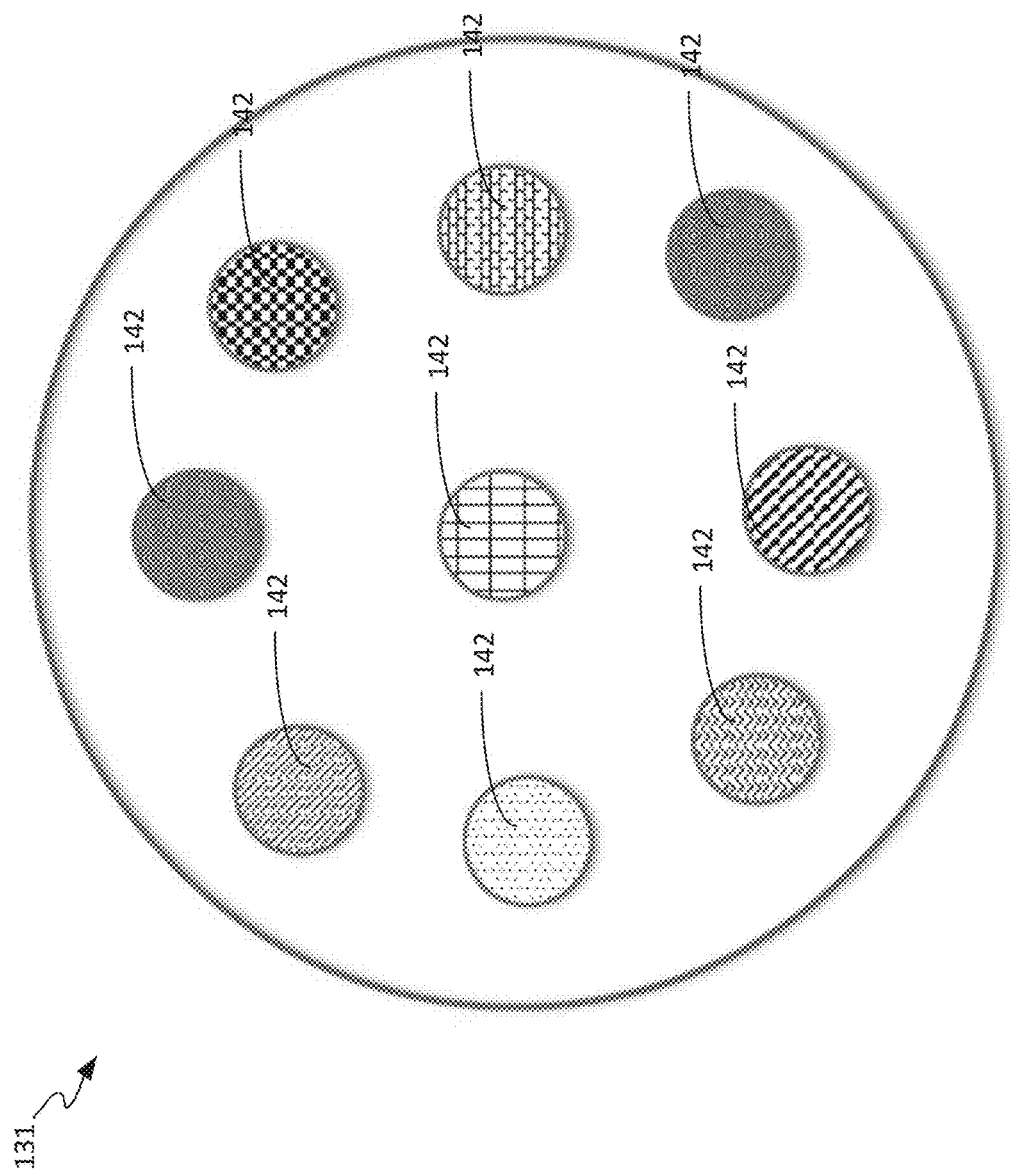
FIG. 4 shows a front plan view of the tissue equivalent phantom shown in FIG. 3 comprising cylindrical dowels that extend through the tissue equivalent phantom shown in FIG. 3 and simulate tissues of different organs of a patient.

FIG. 4 shows a front plan view of the tissue equivalent phantom 131, which comprises cylindrical dowels 142 that extend through the tissue equivalent phantom 131 and simulate tissues of different organs of a patient. Hydrogen rich matter such as water will moderate or slow down the neutrons passing through it. Thus, the gray scale intensity of the neutron image will vary with the hydrogen content in each of the dowels 142 of the phantom 131.

Figure 5:
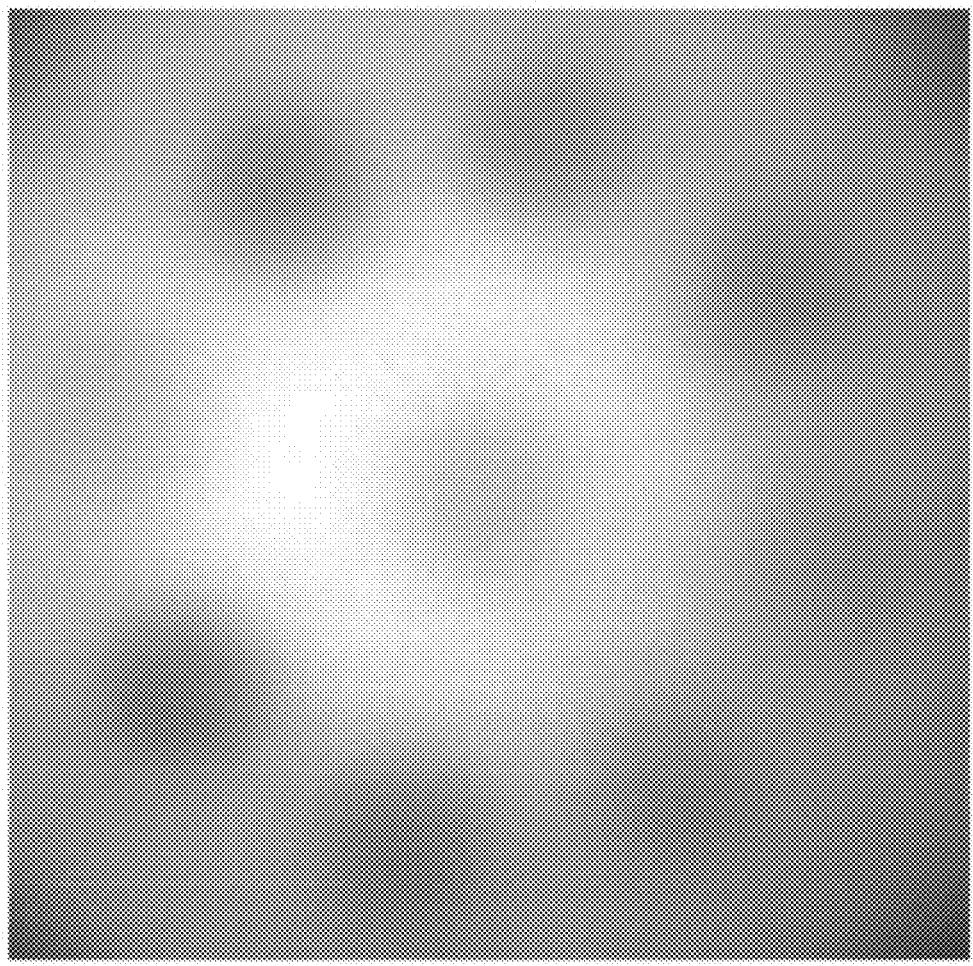
FIG. 5 shows the neutron image of the tissue equivalent phantom shown in FIG. 3 captured by the radiation imager of the imaging system shown in FIG. 3.

FIG. 5 shows the neutron image 150 of the tissue equivalent phantom 131 captured by the radiation imager 106 of the imaging system 130 shown in FIG. 3. The radiation imager 106 acquired this neutron image of the phantom based on the charged particle beam source 101 producing a 10 centimeter (cm)×10 cm beam of protons with average energy of 176 MeV. Although the image is a bit grainy, it does provide useful information that can be used to improve treatment. The neutron moderation effect that determined the gray scale intensity of the neutron image 150 maps to a time-series of 2-D radiographs. This mapping, in turn, relates to the neutron energy deposition in each region of tissue that the neutrons travelled through, and thus to the neutron dose. Discovery of neutron dose hotspots can be utilized as a guidance in subsequent treatments of which tissue regions to avoid or minimize neutron dose exposure in order to minimize secondary cancer risk.

With reference again to FIGS. 2 and 3, the processor 125 and memory device 126 of the imaging systems 120 and 130 are used to perform one or more image processing algorithms that process the images captured by the radiation imager 106 to obtain certain useful information, such as, for example, dose delivered to the target region and/or dose delivered to areas adjacent to the target region. The processor 125 may also perform one or more algorithms that control the timing of image capture by the radiation imager 106 as well as motion of the arm 107 (FIG. 1) in cases where the arm is non-stationary. The processor 125 may also control scanning of the charged particle beam produced by the source 101 in cases in which the charged particle beam is scanned.

For example, because neutron images, which are also referred to herein as radiographic images, are generated using the exit neutrons and/or photons passing through the body of the patient 104, the resulting images may be processed and analyzed by the processor 125 to assess the dose to anatomical structures adjacent to the target region. The radiographic images provide a beam's eye view of regions that the proton beam is incident on, and therefore provide geometrical verification of the proton beam. From this information, known calculations can be used to determine the radiation dose to which the target region and adjacent regions are being exposed. Furthermore, consecutively captured 2-D radiographic images can be analyzed to determine changes in the images over time. Such changes may be caused by patient movement or changes to system parameters, which should not occur but sometimes do. Based on these determinations, the PT session can be modified, corrected or repeated to improve treatment. Additionally, the radiographic images of the patient may be captured in different orientations to reconstruct a three-dimensional (3-D) image by, for example, imparting motion to the arm 127 in a predetermined manner while controlling the timing of image capture by the radiation imager 106 in a predetermined manner. Known reconstruction algorithms can be used or adapted to reconstruct the 3-D images, as will be understood by those of skill in the art in view of the description provided herein.

2-D radiographs can be summed based on the radiation delivered over the entire duration of the proton beam delivery or they can be individual consecutive serial radiographs, each based on delivery of a portion of the proton beam dose. As indicated above, these consecutive serial radiographs can be used to monitor changes in regions of the body through which the proton beam passes. The consecutive serial radiographs can be acquired automatically by programming the optical sensor 114 to capture the images in sequence or by programming the processor 125 to control image capture by the optical sensor 114. In either case, it is unnecessary to pause the beam delivery. Hence a series of 2-D radiographs, differing in time of collection, can be acquired during the beam delivery.

When the imaging system 120 is used in conjunction with a scanning proton beam, it will yield a 2-D radiograph for each axial layer the monoenergetic proton beam stops within and deposits most of its energy. Each layer is associated with a different proton energy, and a treatment beam consists of a range of proton energies that are customized for each patient treatment based on the specific dose distribution required. By combining the 2-D radiographs for each layer, and knowing the proton beam energy used to generate each layer, one can generate a 3-D image of the region of the patient volume irradiated by the proton beam. This volume includes some or all of the SOBP region of the proton beam. This 3-D image can be used to verify the intended delivery of the radiation by comparing this imaging with the treatment planning imaging and radiation dose distribution. In both cases, besides verifying that the proton beam is delivered within the intended patient volume, the imaging can also be carried out on phantoms separately from treatment. In the latter case, adjustments may be made to the treatment plan based on the radiographs that were captured for the phantom.

Furthermore, the radiographs captured by the imaging system 120 can be used to obtain a measure of the spatio-spectral distributions of the forward momentum neutrons, which may be used to optimize the dynamic energy of the optical sensor 114 and to provide additional dose information on secondary neutron-induced cancer risk through neutron imaging using the imaging system 120, which directly related to neutrons generated, their origin and energy distribution, which are all the parameters determining specific neutron dose impact of various patient organs during treatment.

Also, since the neutrons generated will be highly dependent not only on what the characteristics of a specific PT facility are, but also on which type of cancer is being treated and where it is located, the images will allow for significant improvements in patient-by-patient impact and risk. PPI can be used to verify geometric accuracy of the proton beam delivery. This imaging combined with measurements of the neutron spectrum can be used to estimate neutron dose within the patient. The continuous imaging will allow for rapid identification of patient treatment irregularities which would be obtained by the imaging system 120, or post-treatment analysis and corrective action guidance of subsequent treatment for the same patient/tumor.

Figure 6A:
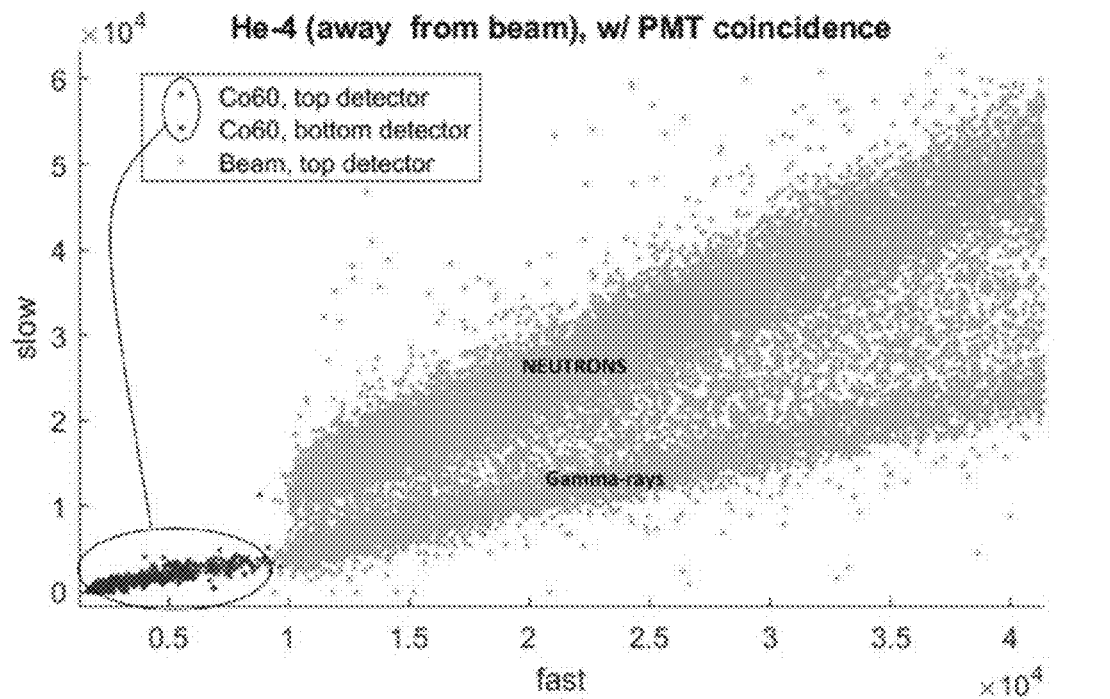
FIGS. 6A and 6B are graphs of neutron spectral distributions that were measured using a He-4 gas detector at different angular locations relative to a water equivalent phantom that was irradiated using a beam of protons with an average energy of 176 MeV.
Figure 6B:
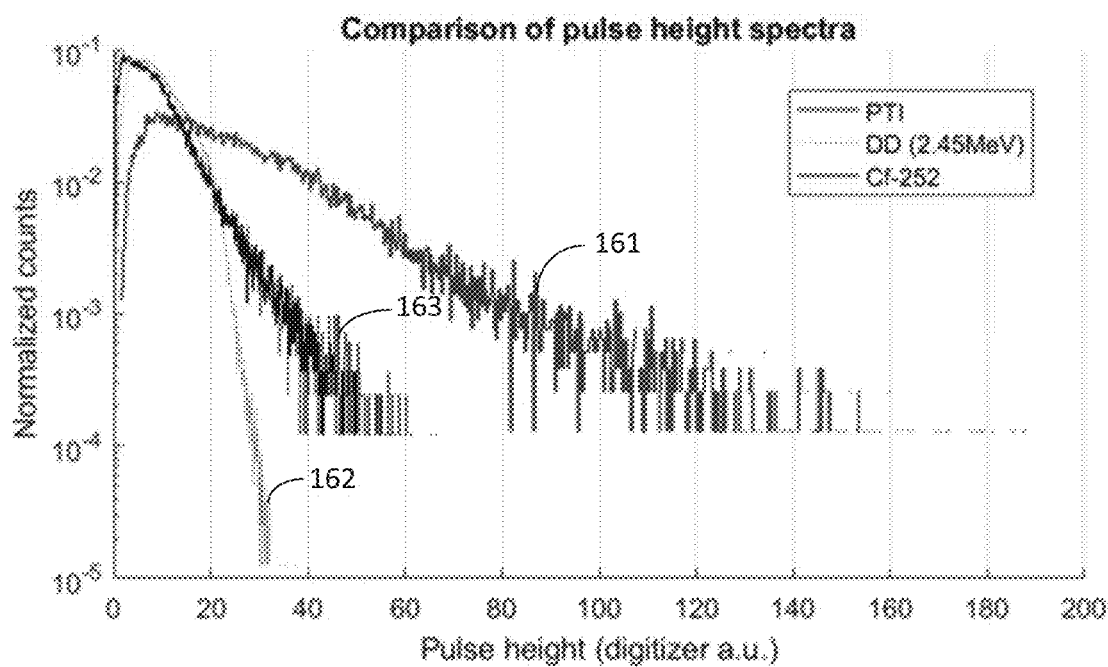

FIGS. 6A and 6B are graphs of the neutron spectral distributions that were measured using a He-4 gas detector at different angular locations relative to a water equivalent phantom that was irradiated using a beam of protons with an average energy of 176 MeV. The results of the measurements indicate the suitability of these detectors for neutron dose verification. FIG. 6A shows the neutron differentiation ability (Pulse Shape discrimination (PSD)) of the proposed system utilizing He-4 noble gas neutron detectors at a PT facility. The radiation environment at a proton irradiation facility is high in dose and of mixed radiation character. The PSD is performed on a pulse-by-pulse basis either in real-time or as post-processing, utilizing pulse integral ratio comparison of prompt and delayed scintillation pulse components induced by neutrons and gamma-rays, respectively. The ability to separate the neutron pulses as shown here over a wide range of energies is essential to proper neutron dose risk evaluation.

FIG. 6B shows the spectroscopic comparison of proton therapy institute (PTI) data (plot 161) with data from other known neutron sources, such as deuterium-deuterium fusion-based neutron generator creating 2.45 MeV neutrons (DD, plot 162), and Californium-252 spontaneous fission source generating neutrons of a wide spectra with average energy 2 MeV (Cf-252, plot 163). The He-4 detector data demonstrates the wide range of detectable neutron energies. When taking into account the energy-dependent neutron dose quality-factors, a direct neutron spectral-dependent detector response of neutron spectra is essential for correct patient-organ neutron-dose estimation. The neutron flux is measured after transport through the patient body, for a scanning particle beam the sequence in time of patient-transmitted neutron spectra obtained in time enable dose calculation of forward affected organs and tissue. For a shaped beam, the same dose calculation would need to utilize the patient-specific phantom that was used to also generate the beam-profile and treatment plan, to obtain the correct dose to the target region and areas adjacent to the target region.

Figure 7:
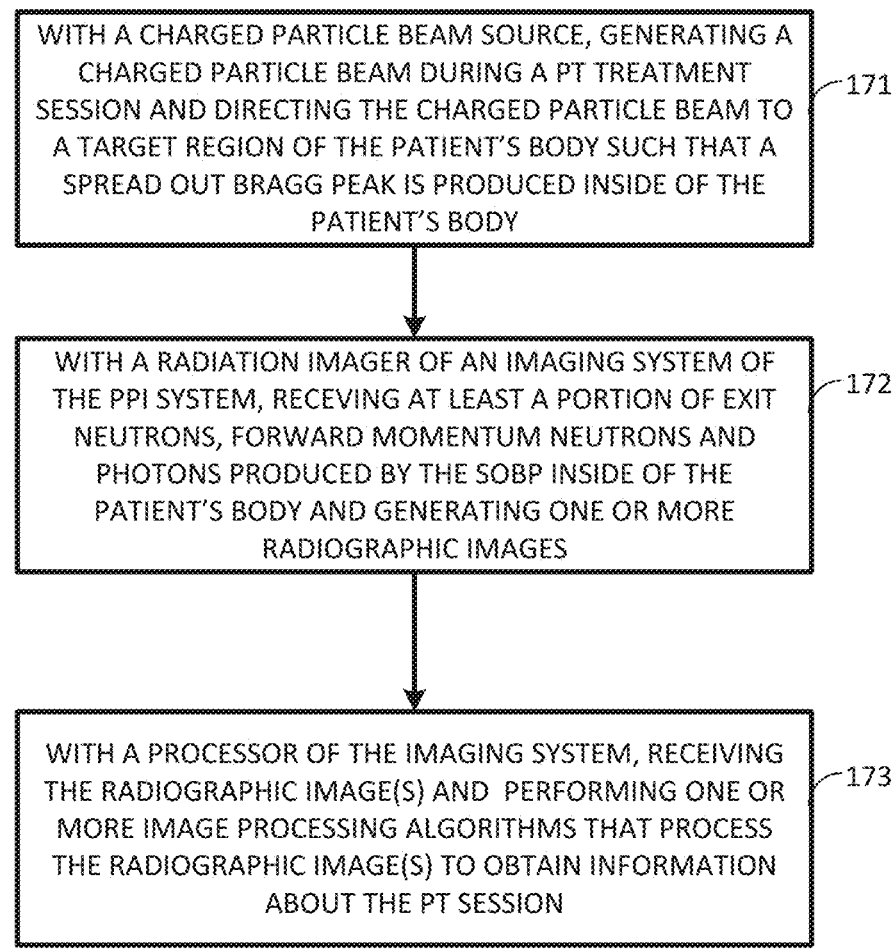
FIG. 7 is a flow diagram of the PPI method in accordance with a representative embodiment.

FIG. 7 is a flow diagram of the PPI method in accordance with a representative embodiment. A charged particle beam source generates a charged particle beam that is directed toward a target region of a body of a patient during a PT session such that an SOBP is produced inside of the patient's body that produces one or more of exit neutrons, forward momentum neutrons and photons, as indicated by block 171. With a radiation imager of an imaging system of the PPI system, at least a portion of the exit neutrons, forward momentum neutrons and/or photons are received and one or more radiographic images are generated from the exit neutrons, forward momentum neutrons and/or photons, as indicated by block 172. With a processor of the imaging system, one or more radiographic images are received and one or more image processing algorithms are performed that process the one or more radiographic images to obtain information about the PT session, as indicated by block 173.

Figure 8:
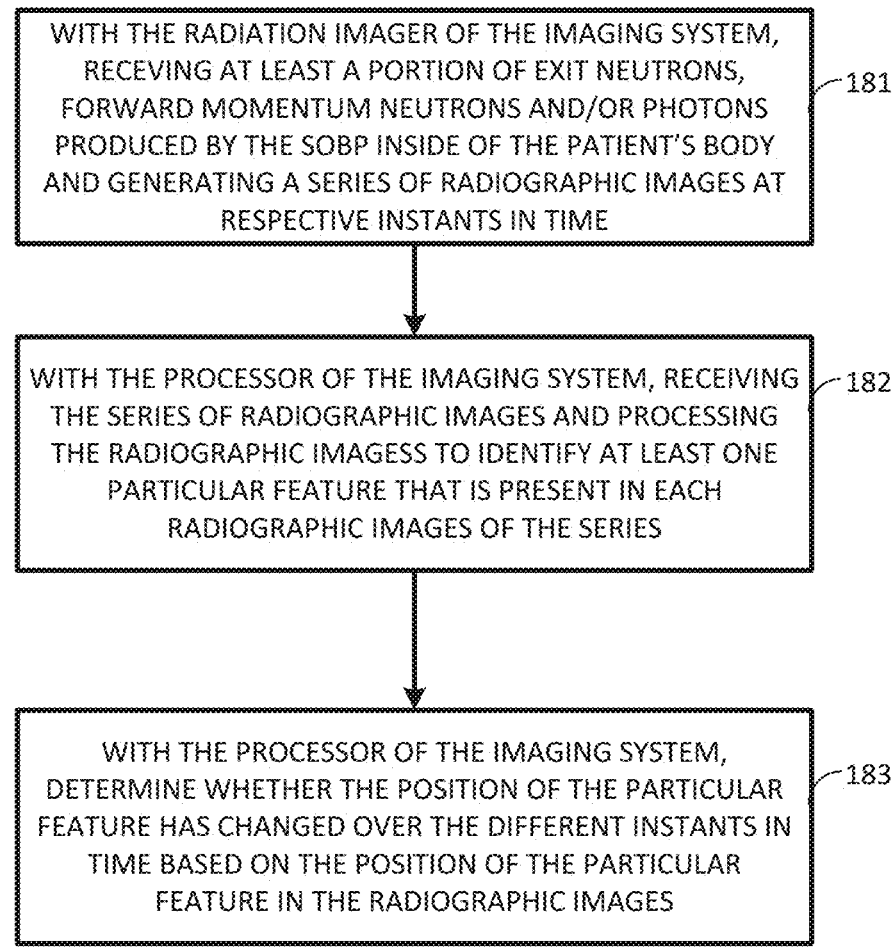
FIG. 8 is a flow diagram representing the PPI method in accordance with one representative embodiment in which the processor shown in FIG. 2 performs a particular image processing algorithm to determine whether the position of the patient has changed during the PT session.

FIG. 8 is a flow diagram representing the PPI method in accordance with one representative embodiment in which the processor 125 performs a particular image processing algorithm to determine whether the position of the patient has changed during the PT session. In accordance with this representative embodiment, the radiation imager generates a series of radiographic images, where each radiographic image of the series is captured at a different instant in time during the PT session, as indicated by block 181. The image processing algorithm performed by the processor 125 analyzes the radiographic images of the series to identify at least one particular feature that is present in each radiographic image of the series, as indicated by block 182. Known feature recognition algorithms may be used for this purpose. Once the particular feature has been identified, the position of the feature within each radiographic image can be used to determine whether the position of the feature has changed over the different instants in time, as indicated by block 183. If a determination is made that the position of the particular feature has changed over time, then this is an indication that the patient's position has likely changed, which may be an indication that the PT session should be repeated or that some change should be made to the treatment plan.

Figure 9:
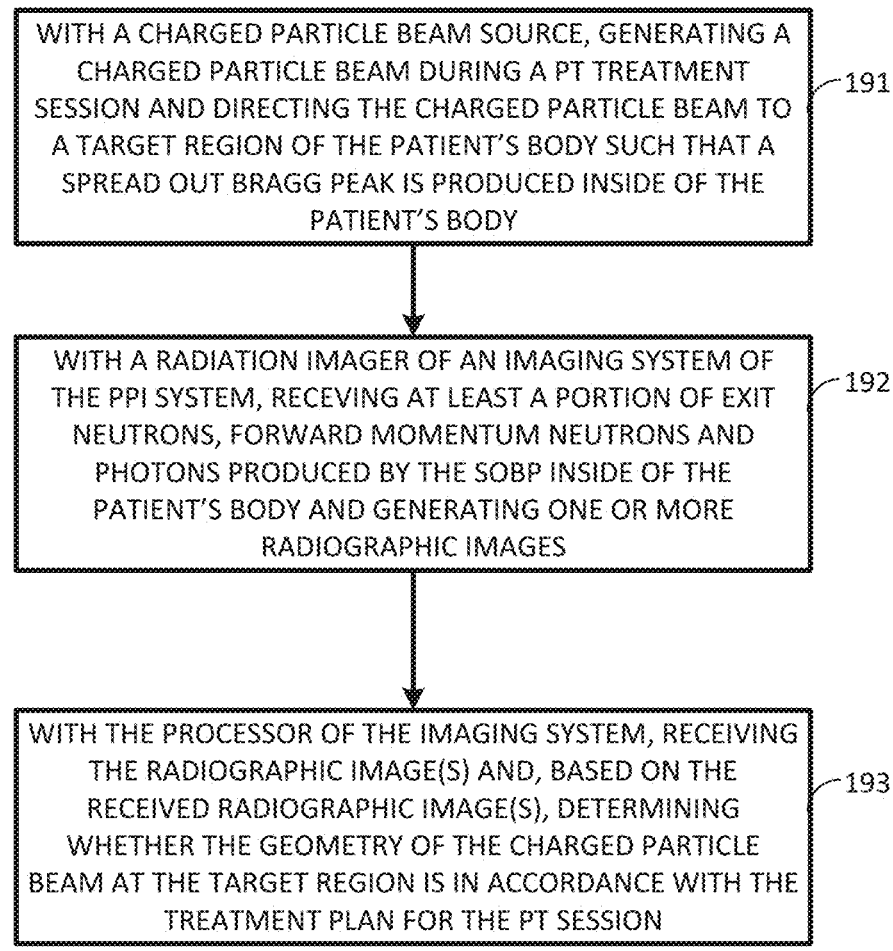
FIG. 9 is a flow diagram representing the PPI method in accordance with another representative embodiment in which the processor shown in FIG. 2 performs a particular image processing algorithm that verifies whether or not the geometry of the charged particle beam at the target region during the PT session is in accordance with the treatment plan.

FIG. 9 is a flow diagram representing the PPI method in accordance with another representative embodiment in which the processor 125 performs a particular image processing algorithm that verifies whether or not the geometry of the charged particle beam at the target region during the PT session is in accordance with the treatment plan. As indicated above, one image processing algorithm that can be performed by the processor analyzes one or more radiographic images to verify that the geometry of the charged particle beam at the target region during the PT session is in accordance with the treatment plan. In FIG. 9, blocks 191 and 192 are identical to blocks 171 and 172, respectively, shown in FIG. 7. At block 193, the processor analyzes one or more radiographic images to verify that the geometry of the charged particle beam at the target region during the PT session is in accordance with the treatment plan. In accordance with this embodiment, the radiographic images can be 2-D or 3-D radiographic images.

Figure 10:
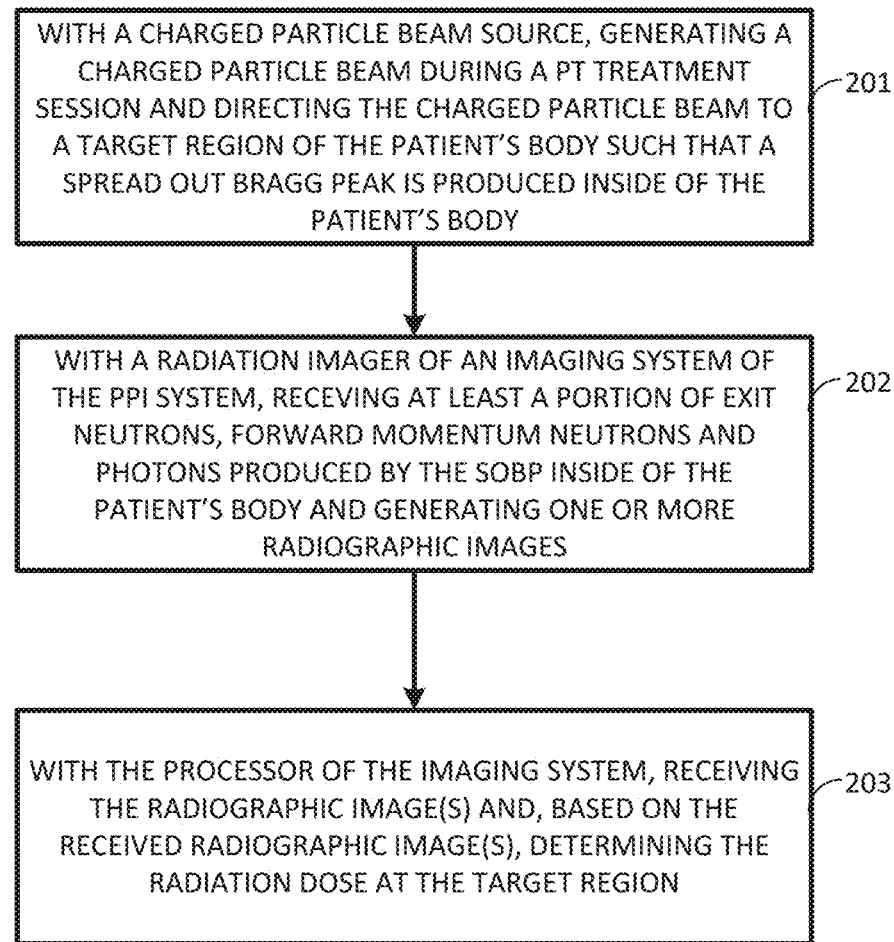
FIG. 10 is a flow diagram representing the PPI method in accordance with another representative embodiment in which the processor shown in FIG. 2 performs a particular image processing algorithm that analyzes one or more radiographic images to determine the radiation dose of the charged particle beam delivered at the target region during the PT session.

FIG. 10 is a flow diagram representing the PPI method in accordance with another representative embodiment in which the processor 125 performs a particular image processing algorithm that analyzes one or more radiographic images to determine the radiation dose of the charged particle beam delivered at the target region during the PT session. As indicated above, one image processing algorithm that can be performed by the processor 125 analyzes one or more radiographic images to determine the radiation dose of the charged particle beam delivered at the target region during the PT session. This can be compared with the treatment plan to determine whether the dose delivered to the target region was is in accordance with the treatment plan. In FIG. 10, blocks 201 and 202 are identical to blocks 171 and 172, respectively, shown in FIG. 7. Block 203 represents the step of the processor analyzing one or more radiographic images to determine the radiation dose of the charged particle beam delivered at the target region during the PT session.

Figure 11:
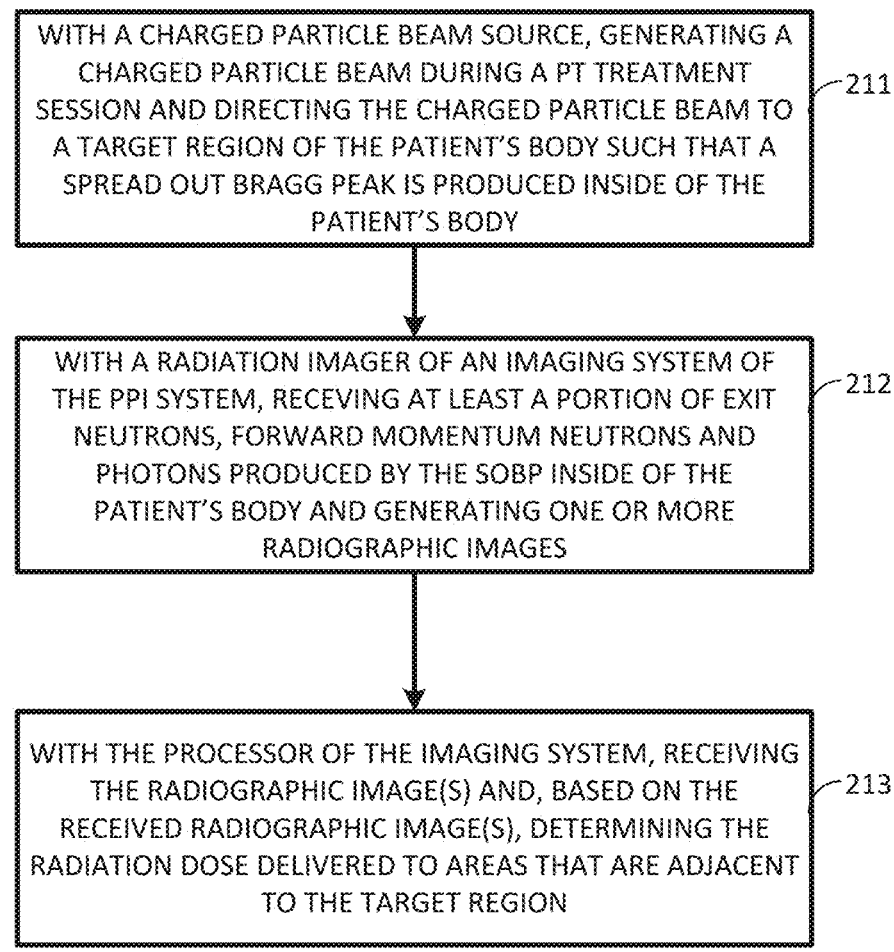
FIG. 11 is a flow diagram representing the PPI method in accordance with another representative embodiment in which the processor shown in FIG. 2 performs a particular image processing algorithm that analyzes one or more radiographic images to determine the radiation dose of the charged particle beam delivered to areas adjacent to the target region during the PT session.

FIG. 11 is a flow diagram representing the PPI method in accordance with another representative embodiment in which the processor 125 performs a particular image processing algorithm that analyzes one or more radiographic images to determine the radiation dose of the charged particle beam delivered to areas adjacent to the target region during the PT session. As indicated above, at least one image processing algorithm performed by the processor can analyze one or more radiographic images to determine the radiation dose of the charged particle beam delivered to areas adjacent to the target region during the PT session. This can be compared with the treatment plan to determine whether to dose delivered to adjacent areas is in accordance with the treatment plan. In FIG. 11, blocks 211 and 212 are identical to blocks 171 and 172, respectively, shown in FIG. 7. Block 213 represents the step of the processor 125 analyzing one or more radiographic images to determine the radiation dose of the charged particle beam delivered to areas adjacent to the target region during the PT session.

Figure 12:
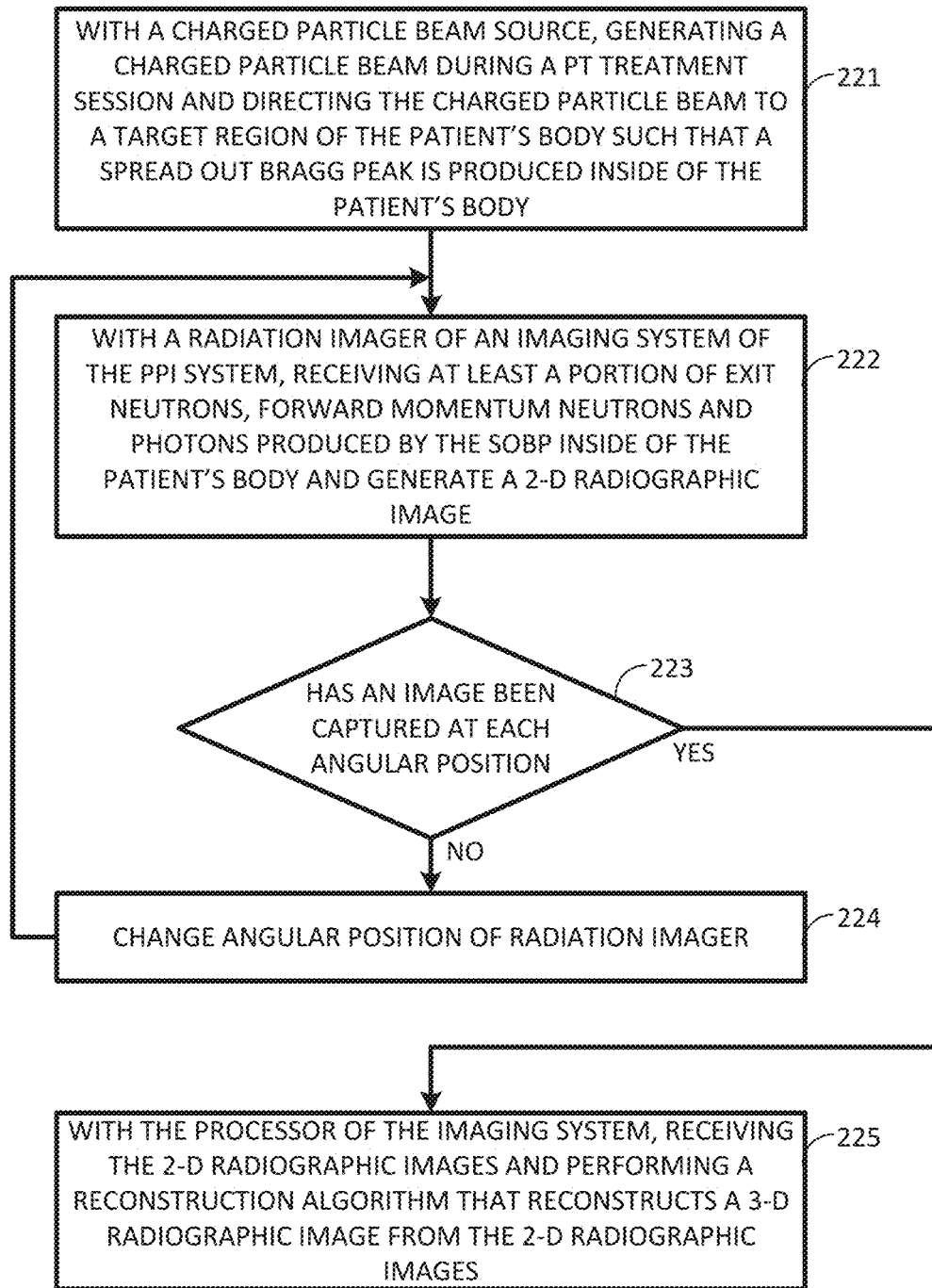
FIG. 12 is a flow diagram representing the PPI method in accordance with another representative embodiment in which the processor shown in FIG. 2 performs a particular image processing algorithm that reconstructs a 3-D radiographic image from a plurality of 2-D radiographic images captured at different angular positions of the radiation imager.

FIG. 12 is a flow diagram representing the PPI method in accordance with another representative embodiment in which the processor 125 performs a particular image processing algorithm that reconstructs a 3-D radiographic image from a plurality of 2-D radiographic images captured at different angular positions of the radiation imager 106. A charged particle beam source generates a charged particle beam that is directed toward a target region of a body of a patient during a PT session such that an SOBP is produced inside of the patient's body that produces one or more of exit neutrons, forward momentum neutrons and photons, as indicated by block 221. With a radiation imager of an imaging system of the PPI system, at least a portion of the exit neutrons, forward momentum neutrons and/or photons are received and at least one 2-D radiographic image is generated from the exit neutrons, forward momentum neutrons and/or photons, as indicated by block 222. Block 223 represents the step of determining whether a 2-D radiographic image has been captured by the radiation imager at each angular position. If not, the angular position of the radiation imager is changed, as indicated by block 224, and the process returns to block 222 where the next 2-D radiographic image is generated at the new angular position. Once an image has been captured at each angular position, as determined at block 223, the process proceeds to block 225 at which the processor 125 performs a reconstruction algorithm that reconstructs a 3-D radiographic image from the plurality of 2-D radiographic images.

Figure 13:
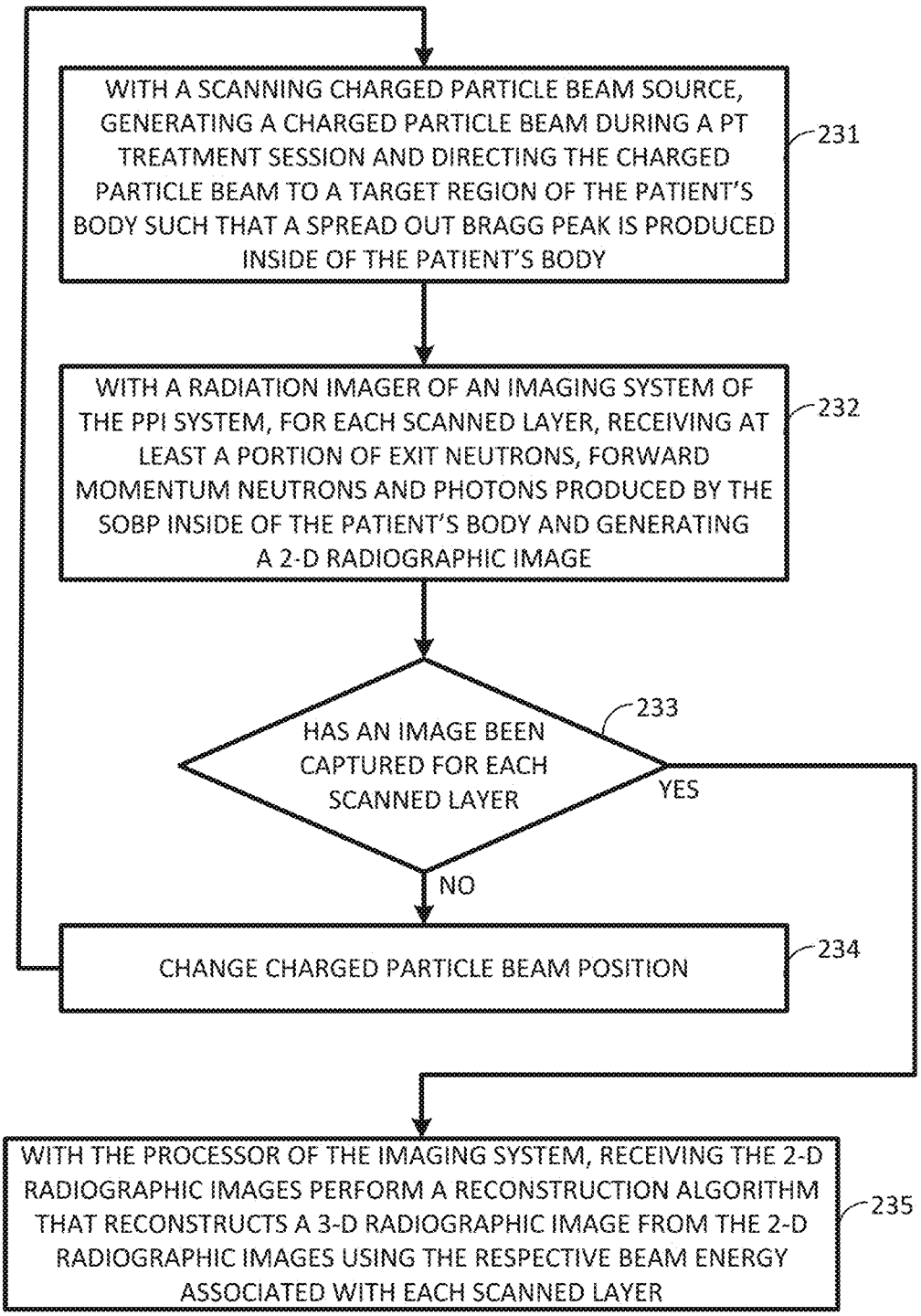
FIG. 13 is a flow diagram representing the PPI method in accordance with another representative embodiment in which the processor shown in FIG. 2 performs a particular image processing algorithm that generates a 2-D radiographic image for each layer of the target region while the charged particle beam is scanned layer by layer.

FIG. 13 is a flow diagram representing the PPI method in accordance with another representative embodiment in which the processor 125 performs a particular image processing algorithm that generates a 2-D radiographic image for each layer of the target region while the charged particle beam is scanned layer by layer and then combines the 2-D radiographs for all of the scanned layers based on the charged beam energy associated with each scanned layer to generate a 3-D radiographic image of the target region. At block 231, the scanning charged particle beam source generates a charged particle beam that is directed toward a target region of a body of a patient during a PT session such that an SOBP is produced inside of the patient's body that produces one or more of exit neutrons, forward momentum neutrons and photons, as indicated by block 231. With the radiation imager, for each scanned layer, at least a portion of the exit neutrons, forward momentum neutrons and/or photons are received and at least one 2-D radiographic image is generated from the exit neutrons, forward momentum neutrons and/or photons, as indicated by block 232. Block 233 represents the step of determining whether a 2-D radiographic image has been captured by the radiation imager for each scanned layer. If not, the charged particle beam position is changed, as indicated by block 234, and the process returns to block 231. Once a 2-D radiographic image has been generated for each layer of the target region, as determined at block 233, the process proceeds to block 235 at which the processor 125 performs a reconstruction algorithm that reconstructs a 3-D radiographic image by combining the plurality of 2-D radiographic images based on the beam energy associated with each respective scanned layer.

Figure 14:
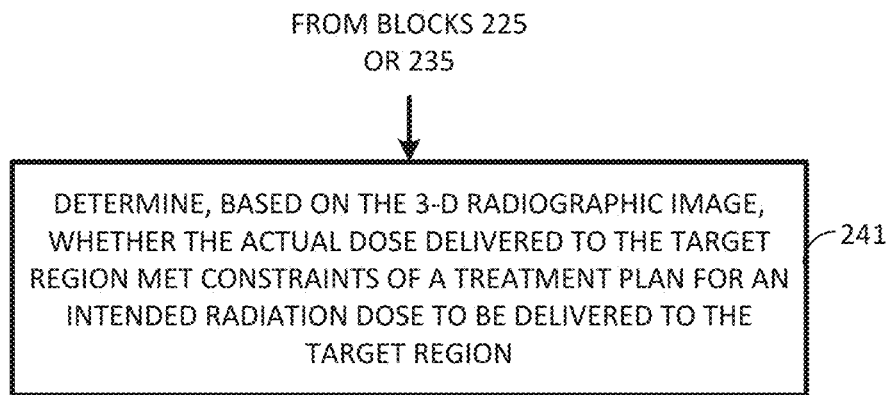
FIG. 14 is a flow diagram representing the PPI method in accordance with another representative embodiment in which the processor shown in FIG. 2 performs a particular image processing algorithm that determines, based on the 3-D radiographic image, whether a radiation dose delivered by the charged particle beam to the target region during the PT session met constraints of a treatment plan for an intended radiation dose to be delivered during the PT session.

FIG. 14 is a flow diagram representing the PPI method in accordance with another representative embodiment in which the processor 125 performs a particular image processing algorithm that determines, based on the 3-D radiographic image, whether a radiation dose delivered by the charged particle beam to the target region during the PT session met constraints of a treatment plan for an intended radiation dose to be delivered during the PT session. The process shown in FIG. 14 can begin from blocks 225 or 235 shown in FIGS. 12 and 13, respectively. Block 241 shown in FIG. 14 represents the step of the processor 125 performing a particular image processing algorithm that determines, based on the 3-D radiographic image, whether the radiation dose delivered by the charged particle beam to the target region during the PT session met constraints of a treatment plan for an intended radiation dose to be delivered during the PT session.

Figure 15:
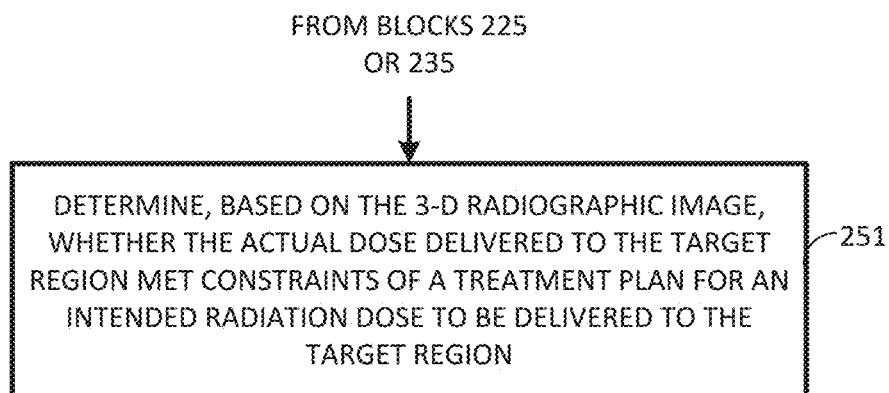
FIG. 15 is a flow diagram representing the PPI method in accordance with another representative embodiment in which the processor shown in FIG. 2 performs a particular image processing algorithm that determines, based on the 3-D radiographic image, whether a radiation dose delivered by the charged particle beam to areas adjacent to the target region during the PT session met constraints of a treatment plan.

FIG. 15 is a flow diagram representing the PPI method in accordance with another representative embodiment in which the processor 125 performs a particular image processing algorithm that determines, based on the 3-D radiographic image, whether a radiation dose delivered by the charged particle beam to areas adjacent to the target region during the PT session met constraints of a treatment plan. The process shown in FIG. 15 can begin from blocks 225 or 235 shown in FIGS. 12 and 13, respectively. Block 251 shown in FIG. 15 represents the step of the processor 125 performing a particular image processing algorithm that determines, based on the 3-D radiographic image, whether the radiation dose delivered by the charged particle beam to adjacent areas to the target region during the PT session met constraints of a treatment plan.

In accordance with a representative embodiment the processor 125 performs a particular image processing algorithm that determines, based on the outcome of one or more of the processes depicted in FIGS. 7-15, whether constraints of a treatment plan are being met during the PT session (if performed in real-time) or whether the constraints were met if the determination is made offline, i.e., after the PT session has been performed.

It should be noted that the algorithms that are performed by the processor 125, such as the image processing algorithms described above, for example, are typically performed in software or firmware that is executed by the processor 125. Such software and/or firmware may be stored in a non-transitory computer-readable medium, such as memory device 126. Some embodiments can be implemented in hardware or in a combination of hardware and software and/or firmware. If implemented in hardware, as in an alternative embodiment, the processor 125 can be implemented with any or a combination of the following technologies, which are all well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

It should be emphasized that the above-described embodiments are merely possible examples of implementations for the purposes of providing a clear understanding of the inventive principles and concepts. Many variations and modifications may be made to the above-described embodiments without departing from the scope of the inventive principles and concepts. All such modifications and variations are intended to be included herein within the scope of this disclosure and the present invention and protected by the following claims.

What is claimed is:

1. A particle portal imaging (PPI) system, comprising:
a radiation imager configured to receive at least a portion of exit neutrons generated by a charged particle beam directed toward a region of a target, the radiation imager comprising:
a converter that receives exit neutrons traveling in a first direction and converts the received exit neutrons into light propagating in the first direction;
at least one mirror or optical fiber that receives at least a portion of the light propagating in the first direction and redirects the received light in a second direction that is different than the first direction; and
an optical sensor configured to receive the light propagating in the second direction and generate at least one radiographic image from the light propagating in the second direction; and
a processor configured to perform one or more image processing algorithms that process the at least one radiographic image to obtain information about the target.

2. The PPI system of claim 1, wherein at least one image processing algorithm analyzes the at least one radiographic image to verify a geometry of the charged particle beam at the region of the target during a charged particle treatment (PT) session.

3. The PPI system of claim 1, wherein at least one image processing algorithm analyzes said at least one radiographic image to determine a radiation dose of the charged particle beam delivered to the region of the target during a charged particle treatment (PT) session.

4. The PPI system of claim 1, wherein at least one image processing algorithm analyzes said at least one radiographic image to determine a radiation dose of the charged particle beam delivered to areas adjacent to the region of the target during a charged particle treatment (PT) session.

5. The PPI system of claim 1, wherein the radiation imager generates a series of radiographic images, each radiographic image of the series of radiographic images being captured at a different instant in time during a charged particle treatment (PT) session.

6. The PPI system of claim 5, wherein at least one image processing algorithm analyzes the radiographic images of the series of radiographic images to identify a feature that is present in the series of radiographic images and to determine whether a position of the feature has changed over the different instants of time.

7. The PPI system of claim 1, wherein the radiation imager is configured to perform a preferential selection process that selects the received exit neutrons that are used to generate said at least one radiographic image based at least in part on energy levels of the received exit neutrons.

8. The PPI system of claim 1, wherein the converter is a scintillator.

9. The PPI system of claim 1, wherein the second direction is at a forty-five-degree angle to the first direction.

10. The PPI system of claim 1, wherein the optical sensor comprises a charge coupled device (CCD) sensor or a complementary metal oxide semiconductor (CMOS) sensor.

11. The PPI system of claim 1, wherein the charged beam source is a proton beam source.

12. A method for particle portal imaging (PPI) system, comprising:
converting, by a converter, exit neutrons traveling in a first direction into light propagating in the first direction, the exit neutrons generated by a charged particle beam directed toward a region of a target;
redirecting, by at least one mirror or fiber optic, at least a portion of the light propagating in the first direction to a second direction that is different than the first direction;
generating, by an optical sensor, at least one radiographic image from the light propagating in the second direction; and
processing the at least one radiographic image, using one or more image processing algorithms implemented by a processor, to obtain information about the target.

13. The method of claim 12, wherein a plurality of two-dimensional (2-D) radiographic images are generated at different respective angles relative to the charged particle beam.

14. The method of claim 13, wherein the one or more image processing algorithms comprises a reconstruction algorithm that generates at least one three-dimensional (3-D) radiographic image from the plurality of 2-D radiographic images.

15. The method of claim 12, wherein the charged particle beam comprises a pencil beam directed through layers of the target, and at least one two-dimensional (2-D) radiographic image is generated for each layer.

16. The method of claim 15, wherein a three-dimensional (3-D) radiographic image of the region of the target it generated based upon the 2-D radiographic images.

17. The method of claim 16, wherein at least one image processing algorithm determines, based on the 3-D radiographic image, whether or not actual delivery of the charged particle beam to the region of the target met constraints of a treatment plan.

18. The method of claim 17, wherein the at least one image processing algorithm modifies, based on the 3-D radiographic image, the treatment plan.

19. The method of claim 12, wherein at least one image processing algorithm determines a radiation dose delivered by the charged particle beam to the region of the target.

20. The method of claim 12, wherein at least one image processing algorithm verifies a geometry of the charged particle beam at the region of the target.

* * * * *